(12) United States Patent
Berner et al.

(10) Patent No.: US 9,993,319 B2
(45) Date of Patent: Jun. 12, 2018

(54) PROCESS FOR PROVIDING STRUCTURES FOR IMPROVED PROTEIN ADHERENCE ON THE SURFACE OF A BODY

(71) Applicant: Straumann Holding AG, Basel (CH)

(72) Inventors: Simon Berner, Basel (CH); Ann Elisabeth Wennerberg, Molndal (SE)

(73) Assignee: STRAUMANN HOLDING AG, Basel (CH)

( * ) Notice: Subject to any disclaimer, the term of this patent is extended or adjusted under 35 U.S.C. 154(b) by 801 days.

(21) Appl. No.: 14/345,445

(22) PCT Filed: Oct. 19, 2012

(86) PCT No.: PCT/EP2012/004380
§ 371 (c)(1),
(2) Date: Mar. 18, 2014

(87) PCT Pub. No.: WO2013/056844
PCT Pub. Date: Apr. 25, 2013

(65) Prior Publication Data
US 2014/0342316 A1 Nov. 20, 2014

(30) Foreign Application Priority Data
Oct. 21, 2011 (EP) .................................... 11008480

(51) Int. Cl.
*A61C 13/00* (2006.01)
*A61K 6/04* (2006.01)
(Continued)

(52) U.S. Cl.
CPC ........ *A61C 13/0007* (2013.01); *A61C 8/0013* (2013.01); *A61C 13/0006* (2013.01); *A61K 6/04* (2013.01); *A61L 27/06* (2013.01); *A61L 27/306* (2013.01); *A61L 27/50* (2013.01); *A61L 2400/12* (2013.01); *A61L 2400/18* (2013.01); *A61L 2430/12* (2013.01)

(58) Field of Classification Search
None
See application file for complete search history.

(56) References Cited

U.S. PATENT DOCUMENTS 6,033,582 A * 3/2000 Lee ..................... A61L 27/3839
204/192.32
6,702,855 B1 * 3/2004 Steinemann ........ A61F 2/30767
623/23.53

(Continued)

OTHER PUBLICATIONS

International Preliminary Report on Patentability and Written Opinion from priority application PCT/EP2012/004380 dated Apr. 22, 2014.

(Continued)

*Primary Examiner* — Shamim Ahmed
(74) *Attorney, Agent, or Firm* — Oliff PLC

(57) ABSTRACT

Process for providing structures for an improved protein adherence on the surface of a body including the steps of a) providing a basic body made of titanium or a titanium alloy,
b) acid-etching the basic body,
c) storing the acid-etched basic body in an aqueous solution, whereby nanostructures are formed on the surface of the basic body, and
d) drying the basic body with the nanostructures formed on its surface.

8 Claims, 15 Drawing Sheets

(51) Int. Cl.
*C23F 1/02* (2006.01)
*C23F 1/38* (2006.01)
*A61L 27/06* (2006.01)
*A61L 27/30* (2006.01)
*A61L 27/50* (2006.01)
*A61C 8/00* (2006.01)

(56) References Cited

U.S. PATENT DOCUMENTS

| | | | | |
|---|---|---|---|---|
| 2004/0049287 | A1* | 3/2004 | Descouts | A61C 8/0012 623/23.6 |
| 2007/0190107 | A1* | 8/2007 | Tosatti | A61L 27/34 424/423 |
| 2009/0061506 | A1* | 3/2009 | Hofer | A61B 5/14546 435/287.9 |
| 2010/0015203 | A1* | 1/2010 | Tengvall | A61L 17/145 424/423 |
| 2010/0179665 | A1* | 7/2010 | Schlottig | A61C 8/0087 623/23.53 |
| 2011/0233169 | A1 | 9/2011 | Mayfield et al. | |

OTHER PUBLICATIONS

International Search Report and Written Opinion dated Nov. 27, 2012 from corresponding International Application No. PCT/EP2012/004380.

Att, et al., "Time-dependent degradation of titanium osteoconductivity: An implication of biological aging of implant materials," Biomaterials, Elsevier Science Publishers BV., Barking, GB, vol. 30, No. 20, Oct. 1, 2009, pp. 5352-5363.

Chih-Yao Chiang, et al., "Formation of TiO2 Nano-network on titanium surface increases the human cell growth," Dental Materials, vol. 25, 2009, pp. 1022-1029.

Her Hsiung Huang, et al., "Blood responses to titanium surface with TiO2 nano-mesh structure," Clinical Oral Implants Research, vol. 23, No. 3, Apr. 4, 2011 pp. 379-383.

Wennweberg, A., et al., "Current knowledge about the hydrophilic and nanostructured SLActive surface," Clinical, Cosmetic and Investigational Dentistry, vol. 3, Sep. 2, 2011, pp. 59-67.

Molenberg, A., et al., "Improved osseointegration of a novel, hydrophilic ti surface—a review," vol. 40, No. 1-2, Jan. 1, 2009, pp. 31-35.

* cited by examiner

Sample 1

Sample 2 (Nacl)

Sample 5 (nano)

Sample 7 (pl.cl.)

Sample 1

Sample 2 (Nacl)

Sample 5 (nano)

Sample 7 (pl.cl.)

Sample 1

Sample 2 (Nacl)

Sample 5 (nano)

Sample 7 (pl.cl.)

Sample 8 (TiZr)

Sample 9 (TiZr NaCl)

Sample 8 (TiZr)

Sample 9 (TiZr NaCl)

PROCESS FOR PROVIDING STRUCTURES FOR IMPROVED PROTEIN ADHERENCE ON THE SURFACE OF A BODY

FIELD OF THE INVENTION

The present invention relates to a process for providing structures for an improved protein adherence on the surface of a body. The invention further relates to a specific body, as well as to the use of said body for an implant, in particular a dental implant.

BACKGROUND

Implants, such as dental implants, are well known in the art. They generally consist of a material, which is biocompatible and which additionally has favourable mechanical properties.

In addition, it is required that the dental implant provides good osseointegration.

The term "osseointegration" designates the direct structural and functional connection between living bone and the surface of the load-bearing implant. A good osseointegration means that the implant, after reaching a primary stability by screwing it into the bone, safely ossifies within a short healing time so that a permanent bond between implant and bone is obtained.

In the infancy of modern implantology a turned, minimally rough surface was the gold standard. Later, an increase to moderately rough surfaces led to faster and firmer osseointegration in several experimental studies using various animal models.

A breakthrough technology in the development of highly osseointegrative dental implants is the so-called "SLA" process, involving sandblasting the implant's surface followed by acid-etching to achieve an optimal topography for the attachment of bone cells.

Based on the "SLA" technology, the so-called "SLActive" surface was developed, which further comprises conditioning the "SLA" surface either in nitrogen or in an isotonic saline solution, thereby maintaining the high hydrophilicity of the "SLA" surface which would otherwise be lost due to reaction with the atmosphere.

SUMMARY OF THE INVENTION

The term "hydrophilic" or "hydrophilicity" as used in the context of the present invention refers to a contact angle of the hydrophilic surface area being less than 90°, more preferably less than 30°, most preferably less than 10°.

Although there is no doubt of the crucial importance of the roughness and of the hydrophilicity of a dental implant for obtaining a good osseointegration, other factors may also play an important role.

In particular, the initial adherence of proteins to the implant's surface during implantation seems also to be of importance, since they have the ability to govern the subsequent cellular response:

When an implant is implanted into tissue, particularly into bone tissue, it is first contacted by water molecules from the surrounding blood. In a next step, ions and proteins will accumulate and adhere on the implant's surface, but without actually penetrating the material. This step is usually referred to as "protein adsorption". It is assumed that the amount and composition of the protein layer formed is decisive for later cell responses.

In this regard it would be desirable to provide "protein retention structures" on the implant's surface, i.e. structures which allow an improved adherence of proteins. "Protein retention structures" which are stable also when stored in a dry environment would be particularly desirable, since this would simplify the packaging of the implant.

The object of the present invention is thus to provide structures for an improved protein adherence on the surface of a body, and in particular of an implant. Thereby, the roughness and hydrophilicity of conventional implants, such as SLActive implants, shall be maintained at least for a certain time frame after its preparation.

The object is solved by the process according to claim 1 and by the body according to claim 7. Preferred embodiments are given in the dependent claims.

The present invention thus relates to a process for providing structures for an improved protein adherence on the surface of a body, said process comprising the steps of
a) providing a basic body made of titanium or a titanium alloy,
b) acid-etching the basic body,
c) storing the acid-etched basic body in an aqueous solution, whereby nanostructures are formed on the surface of the basic body, and
d) drying the basic body with the nanostructures formed on its surface.

According to the process of the present invention, nanostructures are formed on the surface of the basic body.

The term "nanostructures" as used in the context of the present invention means structures extending in at least two dimensions to 200 nm at most. Without wanting to be bound by the theory, these nanostructures form retention sites for the initial adherence of proteins during implantation. Due to this improved protein adherence, an optimal cellular response is obtained ultimately resulting in excellent implant fixation in bone.

The term "aqueous solution" encompasses both pure water as well as a solution in which the solvent is water.

By the process of the present invention, nanostructures are formed on the surface of the basic body. The nanostructures are obtained during storage of the body in the aqueous solution. They are, thus, not formed by a mechanical removing process or by subjecting the surface of the body to other mechanical structuring processes. Rather, the formation of the nanostructures occurs gradually in that they "grow" or "build up" over time.

The body obtained by the present invention is based on titanium or a titanium alloy. In view of its use in the field of implantology, and in particular oral implantology, any suitable grade of titanium or titanium alloy known to the skilled person can be used, including titanium of grade 2 to grade 4.

For titanium made bodies, the presence of TiO, $Ti_2O_2$ and $TiO_2$ at the surface has been reported already. In the context of the present invention, it has now been found that the formation of nanostructures according to the present invention goes along with a higher thickness of a titanium oxide layer which indicates that the composition of the nanostructures is titanium oxide, and in particular $TiO_2$. Specifically, a nominal titanium oxide layer thickness in the range between about 5.5 to about 9.3 nm has been measured by X-ray photoelectron spectroscopy.

It is understood that the process of the present invention encompasses embodiments in which only a portion of the basic body's surface is subjected to steps b) to d) as well as embodiments in which the whole surface is subjected to these steps. Correspondingly, the process allows obtaining structures for improved protein adherence on either the whole surface or only a portion thereof.

All advantages of an SLActive treated body, in particular its hydrophilicity, can likewise be obtained for the body of the present invention at least for a certain time frame.

Most surprisingly, it has been found that the drying of the present invention affects the hydrophilicity of the body's surface only very slowly. Thus, the body of the present invention maintains a relatively high hydrophilicity for a period of up to two months after drying. As the body of the present invention can be stored in a dry environment, very simple packaging of the body is sufficient.

Preferably, the titanium alloy according to step a) is a titanium zirconium (TiZr) alloy, typically comprising Zr in an amount of 13 to 17%.

Titanium zirconium alloys have shown to have a particularly high tensile and fatigue strength (Kobayashi et al., J. Biomed. Mater. Res., 29, 943-950, 1995; Ho et al., J. Mater. Sci. Mater. Med., 19, 3179-3186, 2008). Because they are highly biocompatible with the human body, implants made of a titanium zirconium alloy provide a viable alternative to titanium implants. Studies show that the osteointegrative properties of titanium zirconium implants and titanium implants are very similar (e.g. Grandin et al., Materials 5, 1348, 2012).

Although bodies, specifically implants, made of a titanium zirconium alloy showed formation of fewer and larger nanostructures in comparison to titanium bodies, the amount of adsorbed proteins on TiZr bodies with nanostructures formed thereon showed to be particularly high.

For the acid-etching step according to b), a mixture of $HCl$ and $H_2SO_4$ is typically used.

The storing step according to c) is typically carried out by using a 0.9% NaCl solution, more specifically having a pH of 4 to 6. Likewise, any other suitable aqueous solution can be used including pure water.

According to a preferred embodiment, the storing is carried out for at least two days, more preferably at least three days, most preferably at least two weeks. This is based on the finding that the nanostructures on titanium bodies are detected after two to three days of storing and are completely developed within the first two weeks of storing; no further changes in the nanostructure could be observed for storage times exceeding two weeks.

In the case of bodies made of a TiZr alloy, the storing is preferably carried out for at least two weeks, more preferably at least three weeks.

Prior to the drying according to step d), the basic body with the nanostructures formed on its surface can optionally be rinsed, e.g. by using water or ethanol.

According to a preferred embodiment, after the drying according to step d), the basic body is stored in a dry environment for at least one day, more preferably at least three weeks, most preferably at least four months. In particular, the body is preferably stored in a dry environment for two to six months.

In this context, the term "dry environment", as used in the context of the present invention in particular encompasses a non-aqueous solution and/or a gaseous environment that has a low moisture content. Thus, storage in air, in a gas or mixture of gases, and storage in an organic solvent are encompassed thereby. In case of a gaseous environment, a moisture content of less than 50% is preferred, more preferably of less than 40%, most preferably less than 30%.

The present invention further relates to a body comprising a basic body made of titanium or a titanium alloy and nanostructures formed on the surface of the basic body, said nanostructures comprising titanium oxide.

In particular, the nanostructures comprise $TiO_2$. Preferably, they are at least predominantly in crystalline phase. More preferably, the nanostructures are in an at least approximately purely crystalline phase.

Further, the nanostructures preferably have a needle-like shape indicating that their crystal structure is rutile.

The term "needle-like shape", as used in the context of the present invention in particular encompasses a shape having a ratio of length to diameter (in the following "length-to-diameter ratio") of more than 1:1, particularly of at least 1.5:1, more particularly ranging from 1.5:1 to 4:1. In this context, the diameter is to be understood as the expansion of the nanostructure in a direction perpendicular to the longitudinal direction.

In particular, the term "needle-like shape" encompasses a shape having the basic form of a pyramid-like shape or a cylinder, more particularly a cylinder with a circular cross-section, at least one end of which optionally having a conical or frustoconical shape.

As mentioned above, the nanostructures according to the present invention preferably extend in at least two dimensions to 200 nm at most.

Specifically, the nanostructures preferably have an average diameter of about 5 to 30 nm and an average length of about 20 to 60 nm.

As mentioned, the nanostructures have been found to be stable also under dry storage conditions, allowing very simple packaging of the body without affecting the nanostructure stability.

The body according to the present invention is particularly useful in implantology, and in particular in oral implantology, since the improved osseointegration is of particular importance in this technical field. According to a further aspect, the present invention thus also relates to the use of the body as an implant, in particular a dental implant.

As mentioned earlier, it has been found that improvement of the hydrophilicity of an implant body goes along with improved osteointegrative properties of the implant surface.

Without wanting to be bound by the theory, it is assumed that hydrophilicity of the surface plays a crucial role in the osteointegration process due to an improved attachment of certain proteins (e.g. fibrinogen, plasma fibronectin) and the resulting stabilization of the blood clot. This finally results in the faster formation of new bone.

As will be shown in detail in the context of the examples, the presence of nanostructures on an implant surface significantly enhanced adsorption of proteins after implantation. Best results in terms of high protein adsorption were observed for surfaces which had nanostructures formed thereon and which were also hydrophilic. On such surfaces, the adsorbed proteins showed an almost homogeneous distribution.

It is therefore particularly preferred that the body according to the present invention has further a hydrophilicity defined by a contact angle of less than 90°, more preferably less than 30°, most preferably less than 10°, when contacted with water.

BRIEF DESCRIPTION OF THE DRAWINGS

The images acquired by SEM are given in the attached Figures, of which

FIG. 13 shows a brightness and contrast adjusted fluorescence scanner images of

Figure 14:
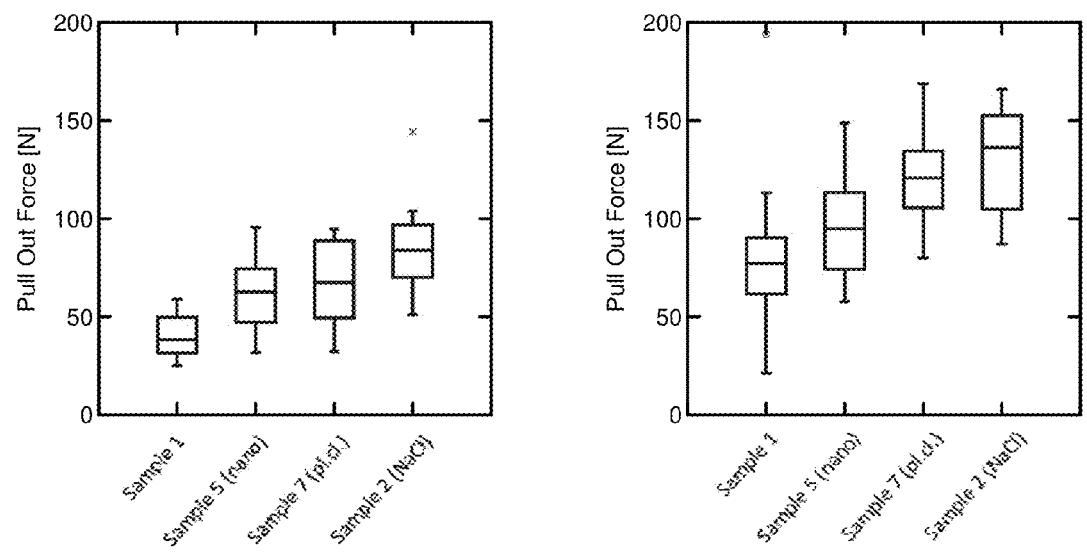
Figure 15:
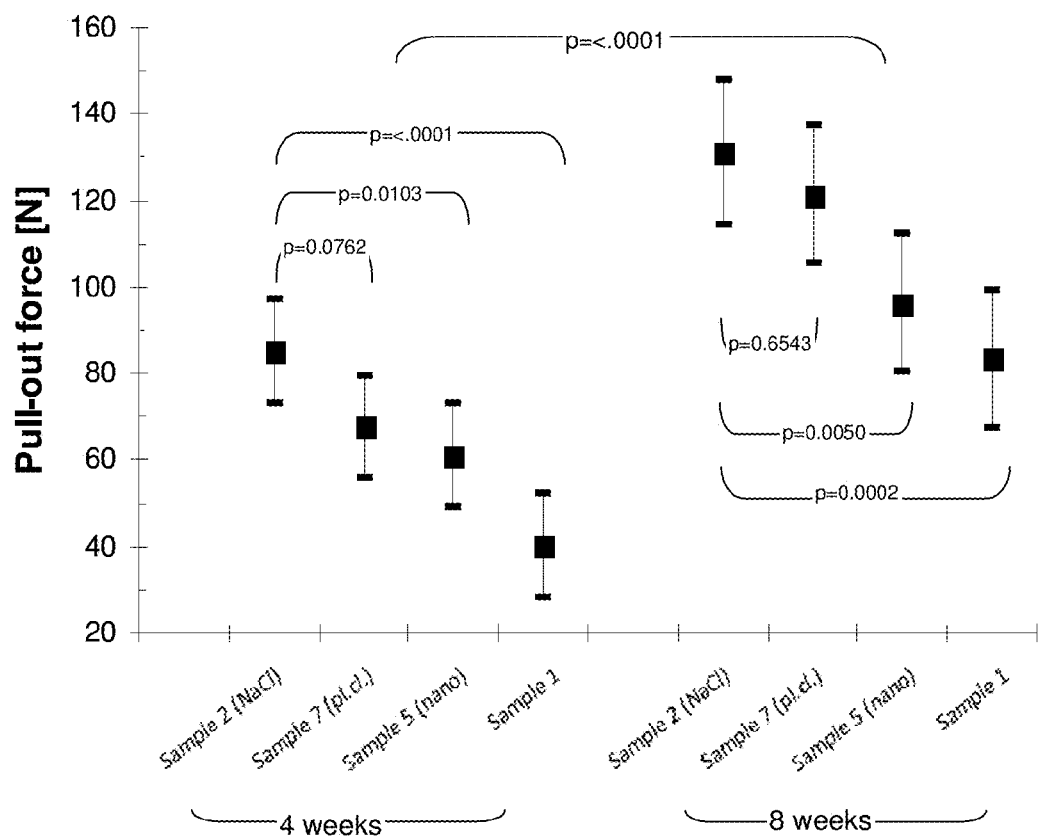

Sample 9 (TiZr NaCl) and Sample 2 (Ti NaCl) surfaces with fibrinogen adsorbed from a 7 µg/ml solution for 10 min, the width of the upper images corresponding to 5 mm and of the lower images corresponding to 1 mm;

FIG. 14 shows a diagram relating to the pull-out-force measured after 4 and 8 weeks of implantation, respectively;

FIG. 15 shows a diagram relating to the pull-out-force measured after 4 and 8 weeks of implantation, respectively.

DETAILED DESCRIPTION

The invention is further illustrated by way of the following Examples:

EXAMPLES

Materials and Methods
Material

Discs, 5 mm in diameter and 1 mm in thickness, were prepared from a c.p. titanium sheet grade 2 and a bimetallic TiZr alloy (13-17% Zr) rod. The Ti discs were degreased in acetone, pickled in a mixture of 2% HF and 10% $HNO_3$ and finally rinsed in pure water prior to further surface modification.

Different surface modifications were investigated besides the commercially available implant surfaces SLA and SLActive (both of Institut Straumann AG, Basel, Switzerland). The influence of the storage media and the surface treatments on the formation of nanostructures was investigated. Polished, acid-etched as well as sandblasted and acid-etched surfaces were analyzed. In addition, samples that have been oxygen plasma cleaned, sandblasted and acid-etched were characterized. Oxygen plasma cleaning is a valuable method to clean surfaces from hydrocarbon contaminations. The resulting surfaces are hydrophilic in case of the Ti or TiZr samples while the oxide layer thickness is only minimally increased compared to untreated samples.

Additionally, biomechanical studies in rabbits were performed to investigate the osseointegration of titanium implant discs in vivo. For these additional studies discs were prepared from a titanium rod grade 4 and provided with a sandblasted and acid-etched surface.

Further Sample Preparation
Titanium Discs

Sample 1: the discs were sand blasted (corundum) with large grits (particle size 250-500 µm), then acid-etched in a boiling mixture of HCl and $H_2SO_4$, followed by cleaning in nitric acid and rinsing in deionised water. Finally the discs were air dried and packed in aluminium foil.

Sample 2 (NaCl): The discs were subjected to the same sand blasting and acid-etching process as for Sample 1, but then further treated under nitrogen cover gas to prevent exposure to air. The discs were rinsed in 0.9% NaCl solution and finally stored in 0.9% NaCl solution at pH 4 to 6.

Sample 3 (water): The discs were prepared like Sample 2 (NaCl) but rinsed and stored in pure water instead of NaCl solution.

Sample 4 (pmod): The discs were treated according to Sample 1 and were subjected to oxygen plasma cleaning and then packed and stored under $N_2$ atmosphere in 0.9% NaCl solution.

Sample 5 (nano): The discs were treated according to Sample 2 (NaCl) and were then aged in NaCl solution for several months. Then the discs were thoroughly rinsed with ultrapure water using an ultrasonic bath. Finally, the discs were air dried and packed in aluminium foil like the Sample 1 discs.

Sample 6 (mod A): The discs were subjected to the same etching procedure as for Sample 1 and Sample 2 (NaCl), but no sand blasting was effected prior to the etching. The steps of rinsing and packaging in 0.9% NaCl solution were the same as for the Sample 2 (NaCl) discs.

Sample 7 (pl.cl.): The discs were treated according to Sample 1 and were subjected to oxygen plasma cleaning before being air dried and packed in aluminium foil.

Titanium Zirconium (TiZr) Alloy Discs (13-17% Zr)

Sample 8 (TiZr): The TiZr discs were prepared like the titanium Sample 1 discs.

Sample 9 (TiZr NaCl): The TiZr discs were prepared like the titanium Sample 2 (NaCl) discs.

Sample 10 (TiZr modMA): The discs were subjected to the same etching procedure as for Sample 8 but machined instead of sand blasted prior to the etching.

All titanium and titanium zirconium alloy discs were γ(gamma)-sterilized (25-42 kGy). Comparison experiments conducted on discs before and after sterilization showed no indication of an influence of the γ(gamma)-sterilization on the results obtained by the following evaluation methods.

Evaluation Methods

Contact Angle Measurements

Contact angle measurements were performed in order to determine the degree of hydrophilicity or hydrophobicity. The contact angles were determined using a sessile drop test with ultrapure water (EasyDrop DSA20E, Krüss GmbH). The water droplets were dosed using an automated unit and a droplet size of 3-6 µl (microliter) was chosen for the samples stored dry and 0.3 µl (microliter) for the samples stored in saline solution. The samples stored in saline solution were blown dry in a stream of Ar prior to the contact angle measurements. The samples stored dry were measured as received. Contact angles were calculated by fitting a circular segment function to the contour of the droplet on the surface.

SEM (Scanning Electron Microscopy)

The visual appearance and morphology of the nanostructures were evaluated with scanning electron microscopy (SEM).

Two different SEM with a cold field emission electron source and an in-lens secondary detector (Hitachi S-4800 with a cold field emission electron source and an in-lens secondary electron detector and Leo Ultra 55) were used. Typically, the images were acquired with an acceleration voltage of 5 kV.

XPS (X-ray Photoelectron Spectroscopy)

Chemical composition of the surface (outermost 5-10 nm), chemical state analysis and oxide layer thickness were investigated with X-ray photoelectron spectroscopy (XPS).

XPS spectra were acquired on a PhI5000 VersaProbe spectrometer (ULVAC-PHI, INC.) equipped with a focused scanning monochromatic Al-Kα(alpha) source (1486.6 eV). The photoelectrons were detected at an angle of 45° to the surface normal by means of a hemi-spherical analyzer with a multi-channel detection system with 16 channels. Each sample was analyzed on one spot with an area of 1.4×0.5 mm². A survey scan and detailed spectra of the elements observed in the survey were acquired.

The samples stored in saline solution were rinsed with ultrapure water and dried in a stream of nitrogen prior to the XPS measurements. The samples stored dry were measured as received.

The oxide layer thickness was calculated using the detailed analysis of the oxidation states of the Ti2p spectrum. The calculation models a homogeneous (in terms of thickness and composition) $TiO_2$ layer on top of metallic titanium.

Fluorescence Intensity Measurements (FSM)/Protein Adsorption Measurements

Albumin (from bovine serum (BSA), Alexa Fluor 647 conjugate, Invitrogen, USA), fibrinogen (from human plasma, Alexa Fluor 546 conjugate, Invitrogen, USA) and fibronectin (Rhodamine Fibronectin (from bovine plasma), Cytoskeleton, Inc., USA) were used as model proteins to study their adsorption behaviour on different surface modifications of Ti, and TiZr surfaces by means of fluorescence microscopy using a fluorescence scanner.

The method applied was based on the application of fluorescently labelled proteins and intensity measurements as well as comparison of fluorescence scanning images.

Albumin and fibrinogen samples were generally immersed into 2 ml of protein solution for 10 min. The adsorption process was carried out in 24-cell well plates. Experiments with fibronectin were carried out in 96-cell well plates and 0.3 ml protein solution but also with an adsorption time of 10 min.

After the immersion in the protein solution, the samples were first transferred into 2 ml of pure buffer followed by five seconds pivoting in another 5 ml of buffer. Then the samples were hold with a tweezer, rinsed first with these 5 ml (by pouring the buffer over the sample) and additionally rinsed for 3 s in a flow of ultrapure water and dried in a stream of nitrogen.

All adsorption experiments were performed at room temperature.

In Table 1, the parameters applied for protein adsorption are shown.

TABLE 1

| Protein | Conc. | Amount of protein solution | Time | Samples |
| --- | --- | --- | --- | --- |
| Albumin | 3 µg/ml | 2 ml | 10 min | All |
| Albumin | 15 µg/ml | 2 ml | 10 s | Sample 1, Sample 2, Sample 5, Sample 7 |
| Fibrinogen | 7 µg/ml | 2 ml | 10 min | All |
| Fibronectin | 3 µg/ml | 0.3 ml | 10 min | All |

Specifically, protein adsorption data was assessed with fluorescence intensity measurements using a microarray fluorescence scanner (Axon Genepix 4200A, Molecular Devices, USA). For intensity read out, the resolution was set to 100 µm pixel$^{-1}$ and only one scan per line was applied in order to minimize bleaching. The gain was adjusted for each protein and was in the range of 400-650.

Imaging with a scan resolution of 5 µm pixel$^{-1}$ and gray value averaging over three scans was applied for studying the lateral adsorption pattern (homogeneity) of the proteins adsorbed.

Table 2 presents the wavelength of the two lasers applied and the absorption/emission wavelength of the protein conjugates tested.

TABLE 2

| Protein | Excitation laser | Protein abs. max. | Scanner filter window | Protein em. max. |
|---|---|---|---|---|
| Albumin | 635 nm | 650 nm | 655-695 nm | 668 nm |
| Fibrinogen | 532 nm | 556 nm | 550-600 nm | 573 nm |
| Fibronectin | 532 nm | 535 nm | 550-600 nm | 585 nm |

Biomechanical Pull-out Measurements

Biomechanical studies in rabbit were performed to investigate the influence of the nanostructures on the osseointegration. The attachment between bone and implant was directly assessed by mechanical testing, in particular by pull-out tests.

For the studies, 25 male and female Swedish loop rabbits at an age of 6-10 months were sedated. During standard surgical procedures, each rabbit received two implants in the proximal-anterior part of tibia. The implants were placed on a platform made on the bone and stabilized with a pre-shaped 0.25 mm titanium band, retained in the cortical bone with two 1.2×3 mm titanium screws. After the implant procedures, the soft tissue layers were repositioned and the wound closed using a resorbable suture. A total of 100 implants were placed in 25 rabbits (n=100, 4 in each animal). One disc-implant was placed upside down. Hence, in total the max. pull-out force value of 99 disc-implants was measured.

Bone-implant attachments were tested 4 and 8 weeks after implantation.

The set-up was adjusted in line and perpendicular with the load-cell using a level tube. The tensile test was performed with an Instron 8511 testing machine (High Wycombe, UK) fitted with a calibrated load-cell of 250 N. Cross-head speed range was set to 1.0 mm/min. Detailed information concerning the surgery procedure as well as the pull-out test description has already been published elsewhere by Rønold et al (Rønold and J. E. Ellingsen, "The use of coin shaped implant for direct in situ measurement of attachment strength for osseointegrating biomaterial surfaces", Biomaterials 23 (2002) 2201).

Results

Contact Angle Measurements

The discs stored dry (Sample 1 and Sample 5) were all hydrophobic, i.e. contact angle >90°. The contact angle on Sample 5 (nano) discs was slightly above 90° while for Sample 1 it was around 130°. However, the hydrophobicity for Sample 5 (nano) increased only very slowly; hydrophilicity was for this sample observed up to 2 months after storage. The samples stored in liquid (Sample 2 (NaCl), Sample 4 (pmod)) were superhydrophilic with contact angles close to zero (Table 3).

TABLE 3

| | disc 1 CA [°] | disc 2 CA [°] | disc 3 CA [°] | mean CA [°] | Std CA [°] |
|---|---|---|---|---|---|
| Sample 1 | 124.4 | 123.3 | 124.1 | 123.9 | 0.6 |
| Sample 2 (NaCl) | 0 | 0 | 0 | 0 | |
| Sample 4 (pmod) | 0 | 0 | 0 | 0 | |
| Sample 5 (nano) | 130.7 | 128.8 | 125.8 | 128.4 | 2.5 |

SEM

The images acquired by SEM are given in the attached Figures, of which

Figure 1A:
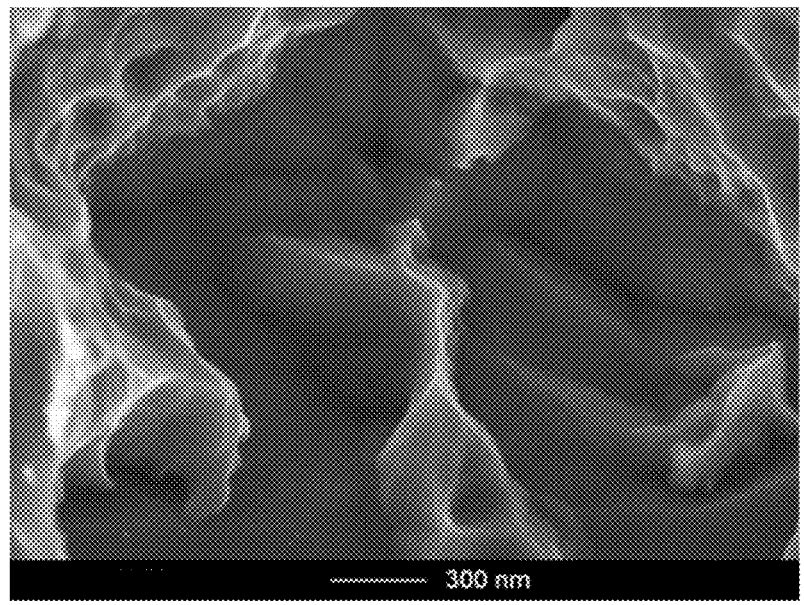
FIG. 1A is an SEM image at about 50 k-magnification of a surface section of a Sample 2 (NaCl) disc before storing.
Figure 1B:
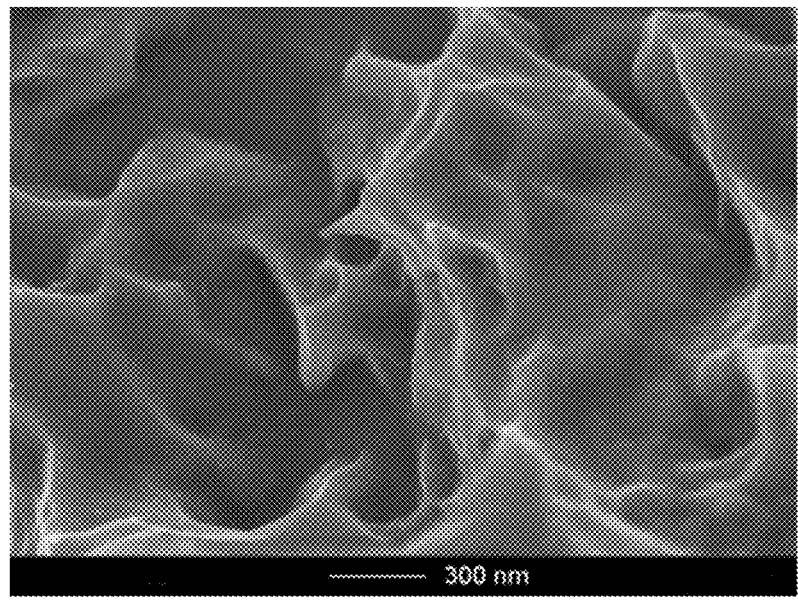
FIG. 1B is an SEM image at about 50 k-magnification of a surface section of a Sample 2 (NaCl) disc after 1 day of storing.
Figure 1C:
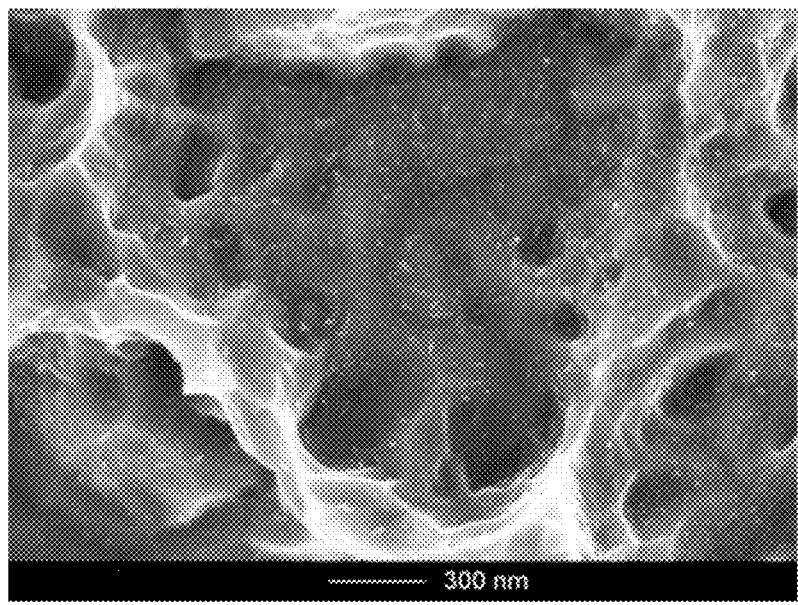
FIG. 1C is an SEM image at 50 k-magnification of a surface section of a Sample 2 (NaCl) disc after 3 days of storing.
Figure 1D:
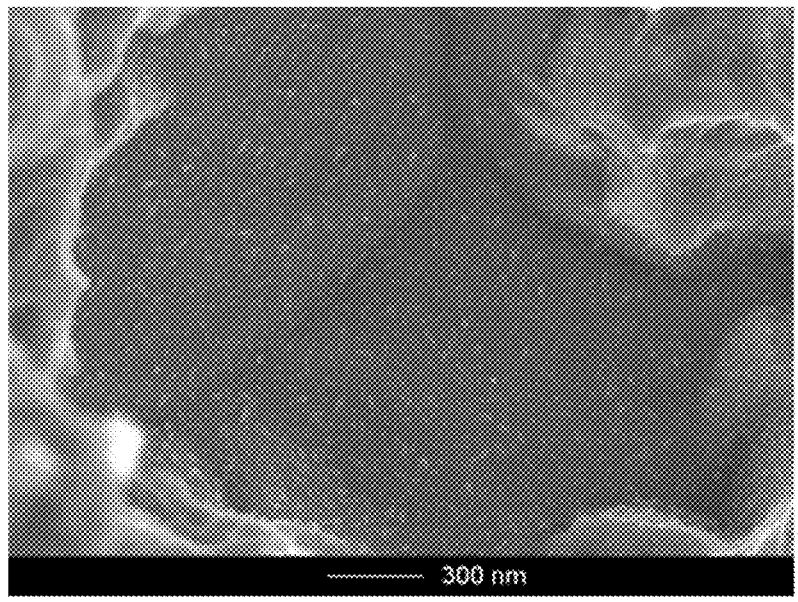
FIG. 1D is an SEM image at 50 k-magnification of a surface section of a Sample 2 (NaCl) disc after 7 days of storing.
Figure 1E:
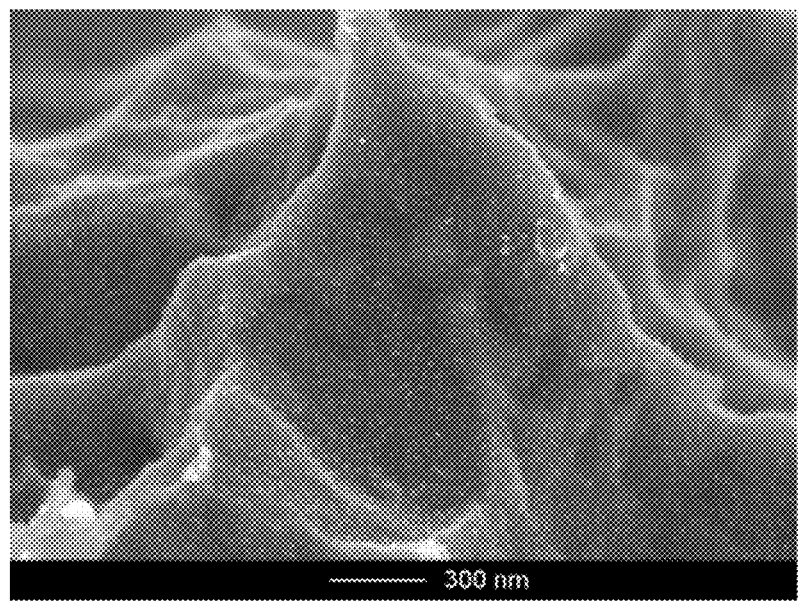
FIG. 1E is an SEM image at 50 k-magnification of a surface section of a Sample 2 (NaCl) disc after 6 months of storing.
Figure 2:
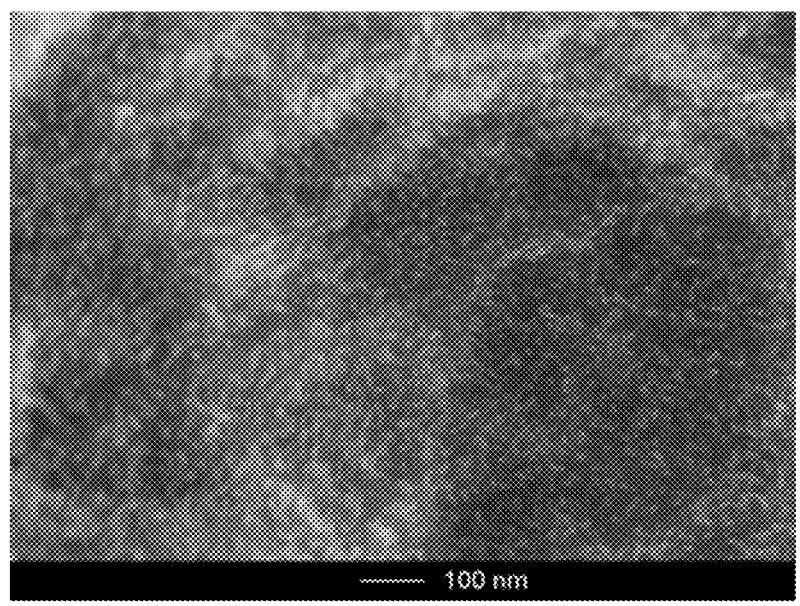
FIG. 2 is an SEM image at 100 k-magnification of a surface section of a Sample 3 (water) disc after 7 months of storing
Figure 3:
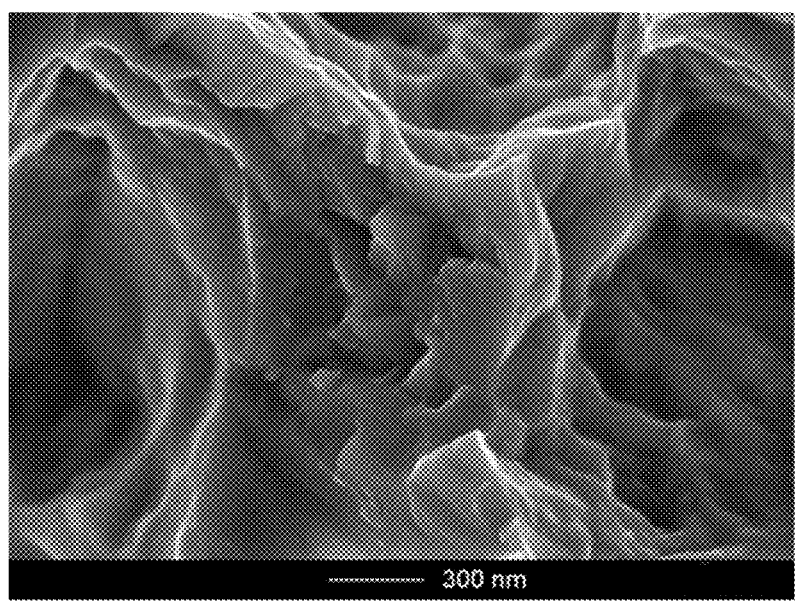
FIG. 3 is an SEM image at 50 k-magnification of a surface section of a Sample 1 disc after 2 months of storing.
Figure 4:
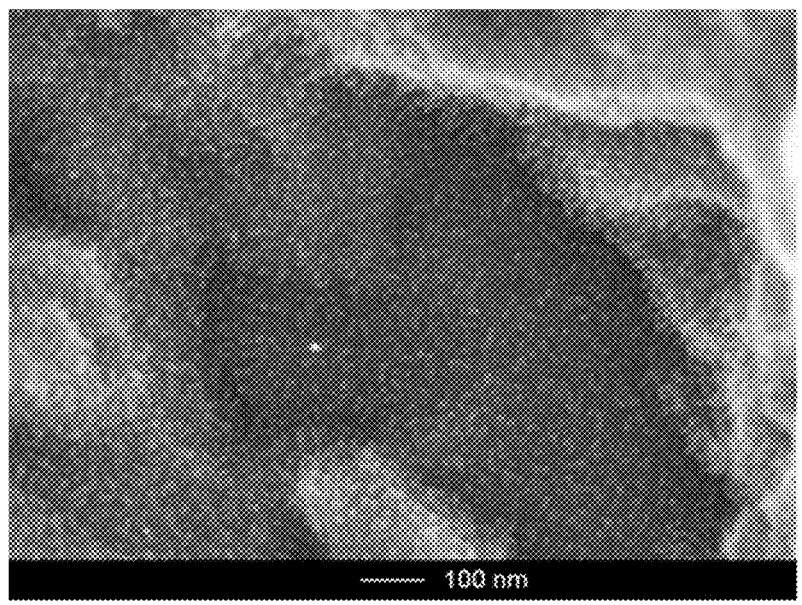
FIG. 4 is an SEM image at 100 k-magnification of a surface section of a Sample 5 (nano) disc after 2 months of storing.
Figure 5A:
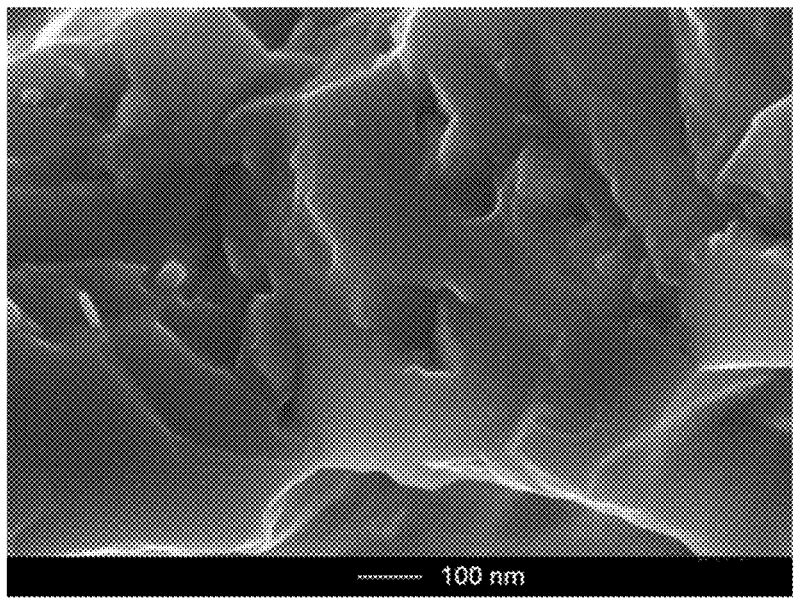
FIG. 5A is an SEM image at 100 k-magnification of a surface section of a Sample 4 (pmod) disc after 2 months of storing.
Figure 5B:
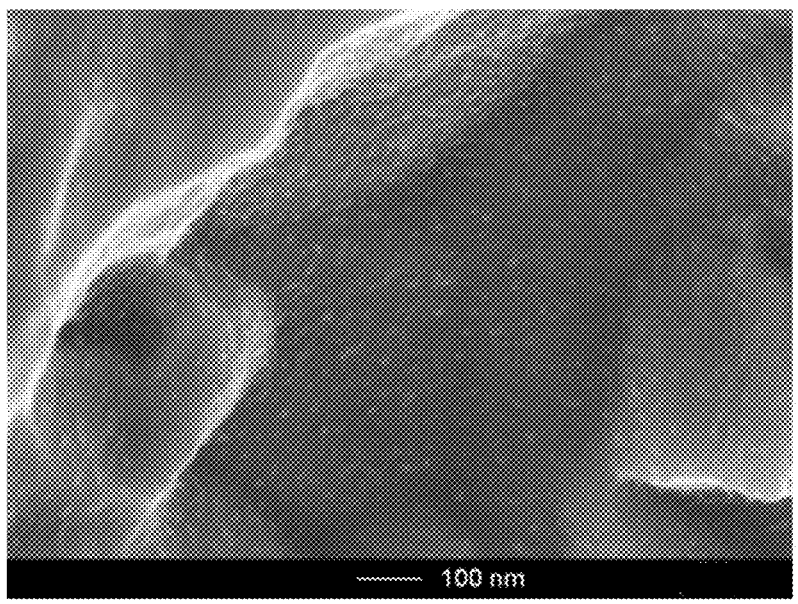
FIG. 5B is an SEM image at 100 k-magnification of a surface section of a Sample 4 (pmod) disc after 9.5 months of storing.
Figure 6:
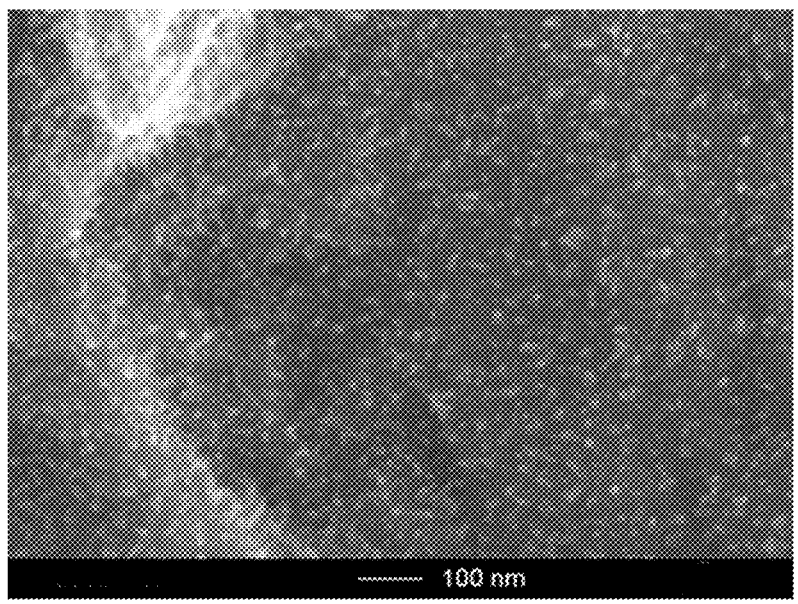
FIG. 6 is an SEM image at 100 k-magnification of a surface section of a Sample 6 (modA) disc after 4 months of storing.
Figure 7A:
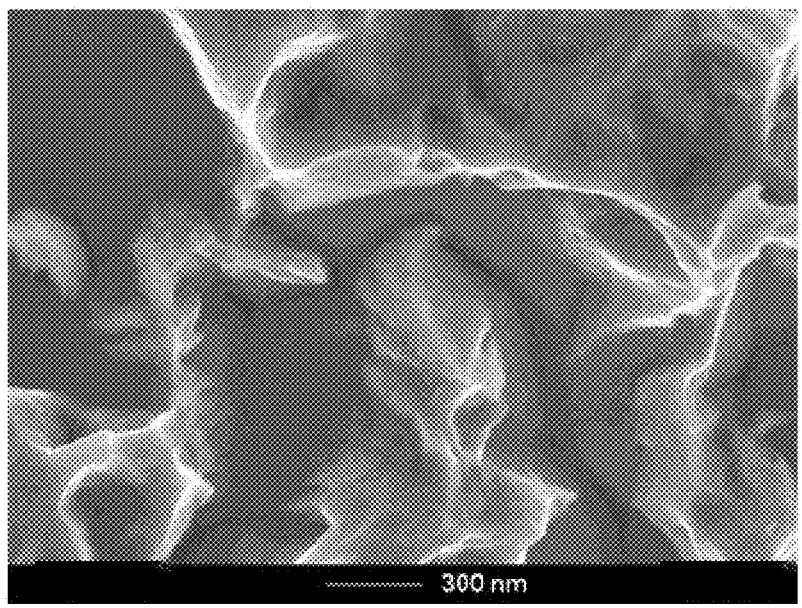
FIG. 7A is an SEM image at 50 k-magnification of a surface section of a Sample 1 disc after 6 months of storing.
Figure 7B:
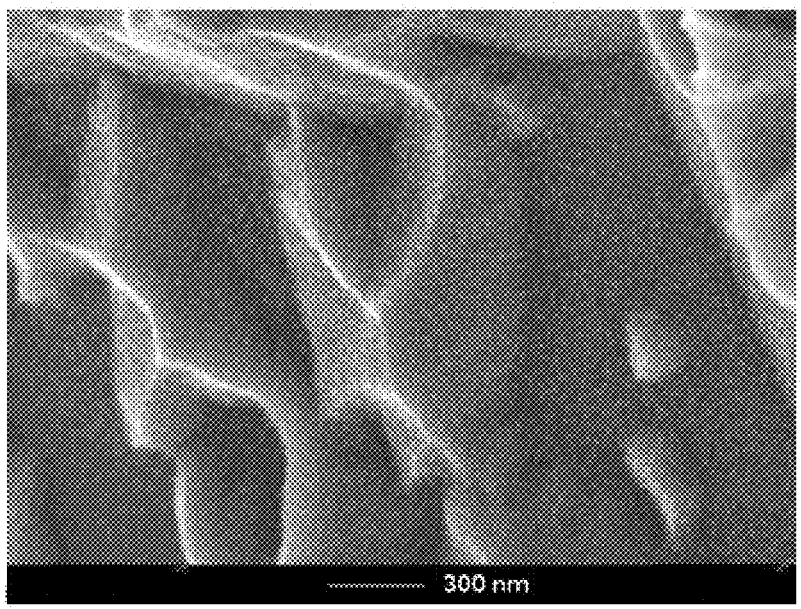
FIG. 7B is an SEM image at 50 k-magnification of a surface section of a Sample 2 (NaCl) disc after 6 months of storing.
Figure 7C:
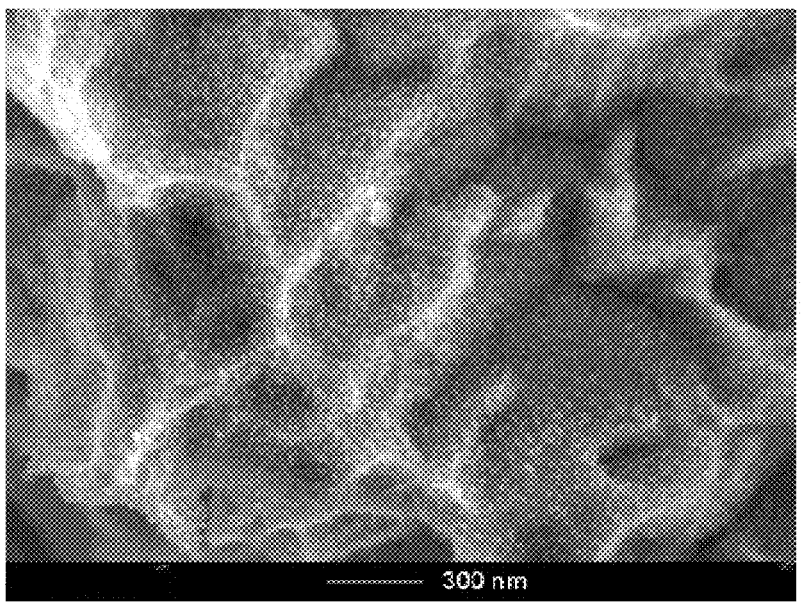
FIG. 7C is an SEM image at 50 k-magnification of a surface section of a Sample 5 (nano) disc after 6 months of storing.
Figure 8A:
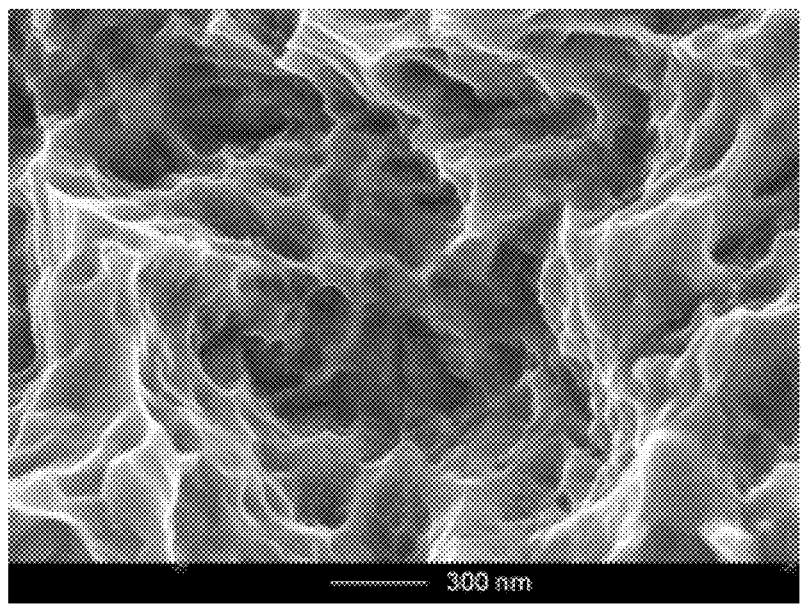
FIG. 8A is an SEM image at 50 k-magnification of a surface section of a Sample 8 (TiZr) disc after 6 months of storing.
Figure 8B:
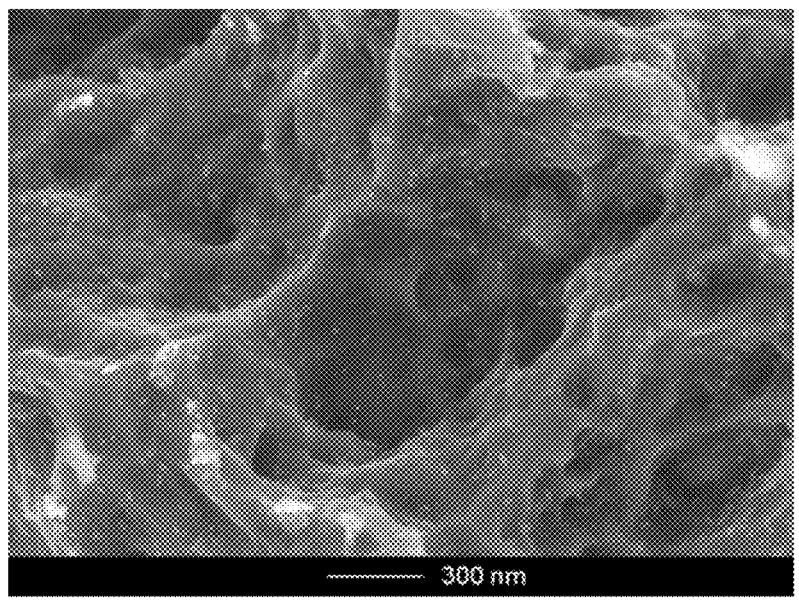
FIG. 8B is an SEM image at 50 k-magnification of a surface section of a Sample 9 (TiZr NaCl) disc after 6 months of storing.

FIG. 1A is an SEM image at about 50 k-magnification of a surface section of a Sample 2 (NaCl) disc before storing;

FIG. 1B is an SEM image at about 50 k-magnification of a surface section of a Sample 2 (NaCl) disc after 1 day of storing;

FIG. 1C is an SEM image at 50 k-magnification of a surface section of a Sample 2 (NaCl) disc after 3 days of storing;

FIG. 1D is an SEM image at 50 k-magnification of a surface section of a Sample 2 (NaCl) disc after 7 days of storing;

FIG. 1E is an SEM image at 50 k-magnification of a surface section of a Sample 2 (NaCl) disc after 6 months of storing;

FIG. 2 is an SEM image at 100 k-magnification of a surface section of a Sample 3 (water) disc after 7 months of storing FIG. 3 is an SEM image at 50 k-magnification of a surface section of a Sample 1 disc after 2 months of storing;

FIG. 4 is an SEM image at 100 k-magnification of a surface section of a Sample 5 (nano) disc after 2 months of storing;

FIG. 5A is an SEM image at 100 k-magnification of a surface section of a Sample 4 (pmod) disc after 2 months of storing;

FIG. 5B is an SEM image at 100 k-magnification of a surface section of a Sample 4 (pmod) disc after 9.5 months of storing;

FIG. 6 is an SEM image at 100 k-magnification of a surface section of a Sample 6 (modA) disc after 4 months of storing;

FIG. 7A is an SEM image at 50 k-magnification of a surface section of a Sample 1 disc after 6 months of storing;

FIG. 7B is an SEM image at 50 k-magnification of a surface section of a Sample 2 (NaCl) disc after 6 months of storing;

FIG. 7C is an SEM image at 50 k-magnification of a surface section of a Sample 5 (nano) disc after 6 months of storing;

FIG. 8A is an SEM image at 50 k-magnification of a surface section of a Sample 8 (TiZr) disc after 6 months of storing; and FIG. 8B is an SEM image at 50 k-magnification of a surface section of a Sample 9 (TiZr NaCl) disc after 6 months of storing;

The evolution of the nanostructures on Sample 2 (NaCl) surfaces was found to be dependent on storage time, the nanostructure being completely evolved after a time frame of about 2 weeks. Immediately after surface modification, no nanostructures were visible (FIG. 1A), after 1 day only very few small structures were detected (FIG. 1B), after 3 days the nanostructures were clearly visible (FIG. 1C), and after 7 days the number of nanoparticles seemed not to increase anymore, however, the particles were still growing in size (FIGS. 1D and 1E). Based on the SEM investigation, on Ti-samples, the nanostructure completely developed within the first two weeks and no further changes in the nanostructures could be observed for storage times exceeding 2 weeks.

After different time points investigated of 2 weeks up to 52 weeks needle-like nanostructures were present on the surfaces stored in water (Sample 3, FIG. 2) and in NaCl solution (Sample 2), whereas such nanoparticles could not be detected on the Sample 1 surface at any of the investigated time points (FIG. 3).

For the Sample 5 (nano) surface SEM clearly demonstrated nanostructures comparable with those on Sample 2 (NaCl) surfaces (FIG. 4). Thus, once formed, nanostructures seem to be stable and not dependent on wet or dry storage condition. The needle-like shape of the nanostructures indicates that their crystal structure is rutile rather than anatase $TiO_2$.

The Sample 4 (pmod) surfaces showed similar appearance as the Sample 1 surfaces and demonstrated only rare occurrence of nanoparticles for short storage periods. However, with increasing storage time nanoparticles appeared on Sample 4 (pmod) discs. Thus the formation of nanostructures can be partly suppressed by oxygen plasma treatment (FIG. 5A, B). Sample 6 (mod A) surfaces (FIG. 6) demonstrated dense nanostructures, similar to those of Sample 2 (NaCl) surfaces.

FIGS. 7A-C are high resolution SEM images of titanium surfaces of A) Sample 1, B) Sample 2 (NaCl) and C) Sample (nano) showing the morphology of the samples at the nanometer scale. Comparing FIG. 7A of Sample 1 with FIGS. 8B and 8C of Sample 2 (NaCl) and Sample 5 (nano), respectively, the formation of needle-like, crystalline nanostructures on Sample 2 (NaCl) and Sample 5 (nano) are clearly visible. The needle-like shape is indicative for the presence of a rutile phase. Surfaces of Sample 2 (NaCl) and Sample 5 (nano) discs show a comparable formation of nanostructures.

FIGS. 8A and 8B showing the morphology of titanium zirconium alloy discs of Sample 8 and Sample 9 (NaCl), respectively, at nanometer scale. FIG. 8B shows nanostructures that are crystalline and have needle-like shape. Surfaces of Sample 2 and Sample 5 (nano) discs show a comparable formation of nanostructures. On TiZr discs, formation of nanostructures was generally slower than on titanium discs and developed within about the first three weeks.

Comparing the figures of Ti (FIGS. 7A, 7B) and TiZr samples (FIGS. 8A, 8B), both showed a similar behaviour in terms of formation and non-formation of nanostructures, respectively: No nanostructure was formed on the hydrophobic discs of Ti Sample 1 (FIG. 7A) and TiZr Sample 8 (FIG. 8A). On the other hand, formation of a distinct nanostructure was observed on hydrophilic discs of Ti Sample 2 (NaCl, FIG. 7B) and TiZr Sample 9 (NaCl, FIG. 8B).

However, the outward appearance of the nanostructures was different on Ti and TiZr samples: As can be seen upon comparison of FIG. 7B (Sample 2, Ti NaCl) with FIG. 8B (Sample 9, TiZr NaCl), nanostructures were observed over the entire surface on the Sample 9 (TiZr NaCl) discs, yet to a much lower density compared with Sample 2 (Ti NaCl). The nanoparticles on Sample 9 (TiZr NaCl) were also larger than those on the Sample 2 (Ti NaCl) surface.

Table 4 gives a summary of the presence of the nanostructure on the different types of surfaces.

TABLE 4

| Surface | Nanostructure | Hydrophilic |
|---|---|---|
| 1. Sample 1 | no | no |
| 2. Sample 2 (NaCl) | yes | yes |
| 3. Sample 3 (water) | yes | yes |
| 4. Sample 4 (pmod) | No (for short storage periods) | yes |
| 5. Sample 5 (nano) | yes | slow decrease during storage in dry environment |
| 6. Sample 6 (mod A) | yes | yes |
| 7. Sample 7 (pl. cl.) | no | yes |
| 8. Sample 8 (TiZr) | no | no |
| 9. Sample 9 (TiZr NaCl) | yes (but fewer and larger structures) | Yes |

TABLE 4-continued

| Surface | Nanostructure | Hydrophilic |
|---|---|---|
| 10. Sample 10 (TiZr modMA) | yes | yes |

XPS

The chemical composition is shown in Table 5. The carbon level was clearly higher for Sample 1 and Sample 5 (nano) discs than for those samples stored in liquid. The chemical compositions of the latter (Sample 2 (NaCl) and Sample 4 (pmod), both stored in NaCl and Sample 3 stored in water) were similar. The presence of aluminium is explained by $Al_2O_3$ residues from the blasting process. The chemical composition of Sample 9 (TiZr NaCl) was comparable to Sample 2 (NaCl), but due to the base material Zr was additionally observed. In addition, trace amounts of F were present on Sample 9 (TiZr NaCl), and trace amounts of Na were found on Sample 5 (nano).

Table 5 shows the apparent normalized (sum equals 100%) atomic concentrations [%] of the elements detected by XPS. The average values of three samples per group are presented.

TABLE 5

| Sample | O | Ti | N | C | P | Al | F | Zr |
|---|---|---|---|---|---|---|---|---|
| 1. Sample 1 | 45.0 | 17.5 | 1.7 | 34.9 | 0.1 | 0.8 | | |
| 2. Sample 2 (NaCl) | 61.1 | 27.1 | 1.6 | 8.2 | 0.1 | 1.9 | | |
| 3. Sample 3 (water) | 64.8 | 27.5 | 1.5 | 4.8 | | 1.5 | | |
| 4. Sample 4 (pmod) | 60.2 | 24.2 | 0.9 | 10.5 | 0.7 | 3.6 | | |
| 5. Sample 5 (nano) | 48.1 | 18.5 | 1.4 | 30.3 | 0.2 | 1.3 | | |
| 6. Sample 6 (mod A) | 61.9 | 25.6 | 1.7 | 7.2 | 0.0 | 1.5 | | |
| 7. Sample 7 (pmod P) | 54.6 | 20.9 | 1.2 | 20.2 | | 2.1 | | |
| 8. Sample 9 (TiZr NaCl) | 60.4 | 23.4 | 0.8 | 7.6 | 0.0 | 3.6 | 0.7 | 3.5 |

The evaluation of oxide states demonstrated the presence of TiO, $Ti_2O_3$ and $TiO_2$ besides the metallic Ti state. The nominal thickness of the $TiO_2$ layer varied from 5.5 to 9.3 nm. For those samples stored in NaCl, the thickness of the $TiO_2$ layer was found to correlate to the nanostructure formation.

A comparable thickness of the $TiO_2$ layer was observed for the samples with the nanostructure (Sample 2 (NaCl), Sample 5 (nano), Sample 3 (water), Sample 6 (mod A) and Sample 9 (TiZr NaCl)). These samples showed the thickest oxide layer, while the Sample 4 (pmod) and Sample 7 (pmod P) surfaces showed a clearly lower oxide layer thickness. The lowest oxide layer thickness was observed for the Sample 1 discs (Table 6).

TABLE 6

| Sample description | Ti 2p3 met [%] | Ti 2p3 TiO [%] | Ti 2p3 $Ti_2O_3$ [%] | Ti 2p3 $TiO_2$ [%] | d [nm] | Std d [nm] |
|---|---|---|---|---|---|---|
| 1. Sample 1 | 7.2 | 6.8 | 4.0 | 82.0 | 5.5 | 0.1 |
| 2. Sample 2 (NaCl) | 1.3 | 2.6 | 1.7 | 94.4 | 9.3 | 0.1 |

TABLE 6-continued

| Sample description | Ti 2p3 met [%] | Ti 2p3 TiO [%] | Ti 2p3 Ti$_2$O$_3$ [%] | Ti 2p3 TiO$_2$ [%] | d [nm] | Std d [nm] |
|---|---|---|---|---|---|---|
| 3. Sample 3 (water) | 1.5 | 1.7 | 2.2 | 94.6 | 9.0 | 0.1 |
| 4. Sample 4 (pmod) | 3.2 | 2.7 | 2.0 | 92.2 | 7.4 | 0.2 |
| 5. Sample 5 (nano) | 1.5 | 2.7 | 1.7 | 94.1 | 9.1 | 0.1 |
| 6. Sample 6 (modA) | 1.7 | 3.3 | 0.0 | 95.1 | 8.9 | 0.2 |
| 7. Sample 7 (pmodP) | 3.2 | 1.6 | 2.4 | 92.9 | 7.5 | 0.5 |
| 8. Sample 9 (TiZr NaCl) | 1.8 | 1.8 | 2.7 | 93.7 | 8.7 | 0.2 |

Fluorescence Intensity Measurements (FSM)/Protein Adsorption Measurements

Figure 9:
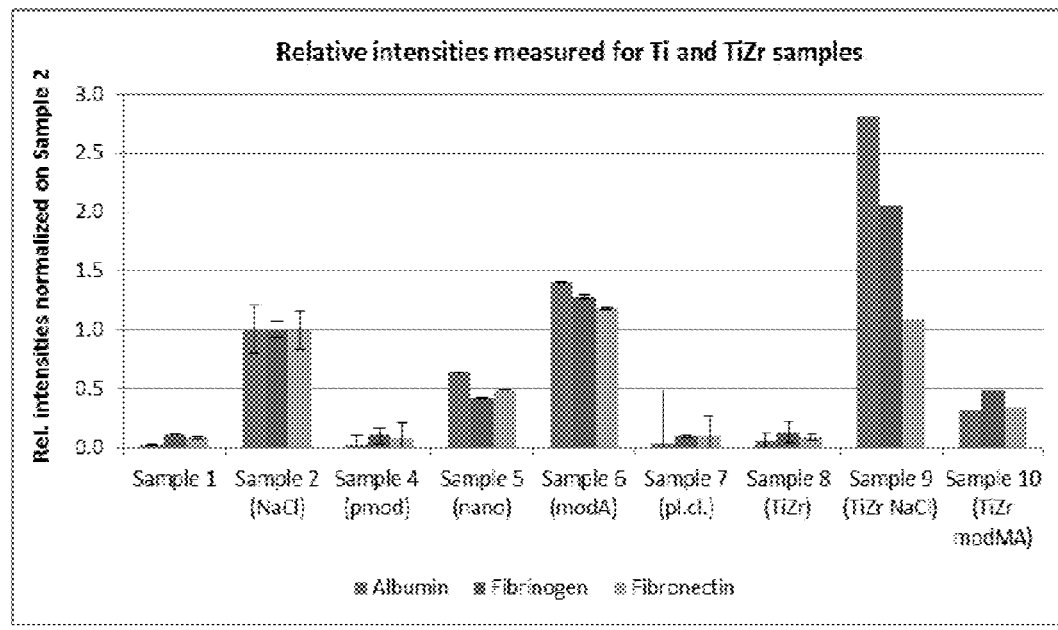
FIG. 9 shows a diagram relating to the intensities normalized on Sample 2 (NaCl) measured for albumin, fibrinogen and fibronectin on various Ti and TiZr surfaces.
Figure 10:
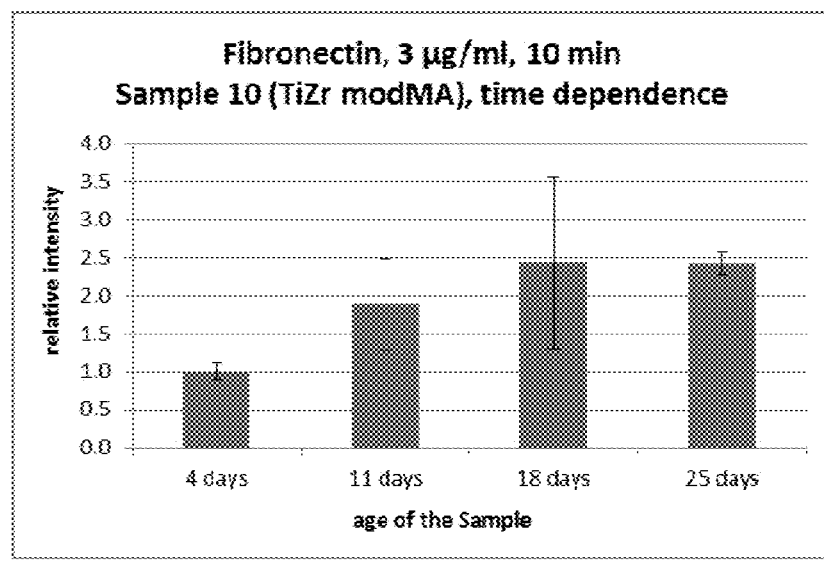
FIG. 10 shows a diagram relating to the development of the fibronectin fluorescence intensity measured on Sample 10 surfaces (TiZr modMA) over three weeks. Samples were produced 4 days prior to the first measurement of the time series.
Figure 11A:
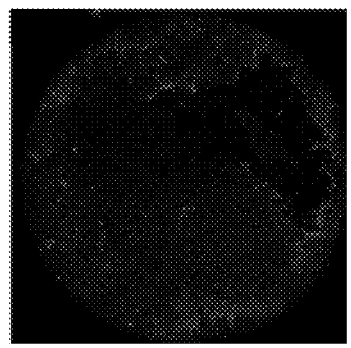
FIG. 11A shows high resolution (5 µm) fluorescence scanner images of albumin adsorbed on hydrophobic (Sample 1, Sample 5 (nano)) and hydrophilic (Sample 2 (NaCl), Sample 7 (pl.cl.)) titanium surfaces with nanostructures (Sample 5 (nano), Sample 2 (NaCl)) and without nano-structures (Sample 1, Sample 7 (pl.cl.))
Figure 11A:
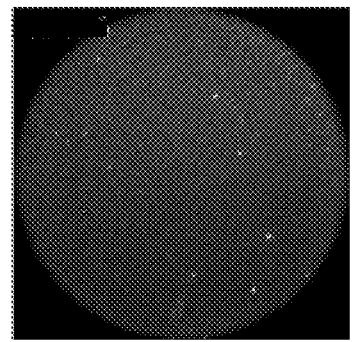
Figure 11A:
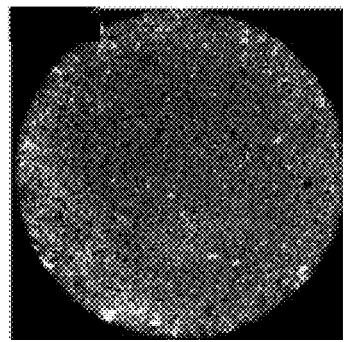
Figure 11A:
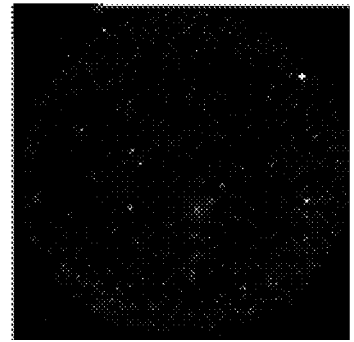
Figure 11B:
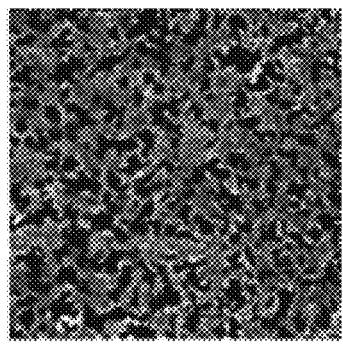
FIG. 11B shows a magnification of the high resolution (5 µm) fluorescence scanner images of FIG. 11A (width of image corresponds to 1 mm)
Figure 11B:
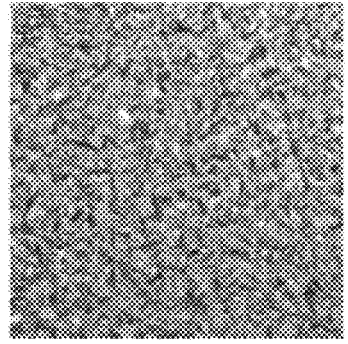
Figure 11B:
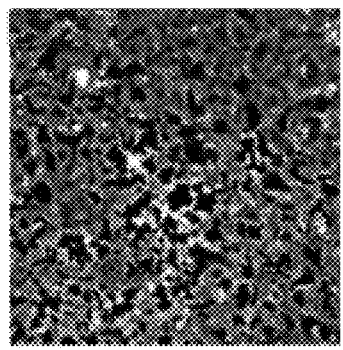
Figure 11B:
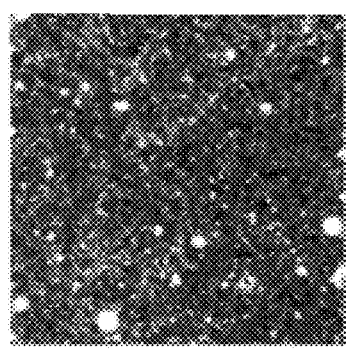

For each surface modification and examined protein, three samples were measured. The fluorescence intensity data acquired by FSM and the images acquired by fluorescence scanning are given in the attached Figures, of which FIG. 9 shows a diagram relating to the intensities normalized on Sample 2 (NaCl) measured for albumin, fibrinogen and fibronectin on various Ti and TiZr surfaces;

FIG. 10 shows a diagram relating to the development of the fibronectin fluorescence intensity measured on Sample 10 surfaces (TiZr modMA) over three weeks. Samples were produced 4 days prior to the first measurement of the time series;

FIG. 11A shows high resolution (5 µm) fluorescence scanner images of albumin adsorbed on hydrophobic (Sample 1, Sample 5 (nano)) and hydrophilic (Sample 2 (NaCl), Sample 7 (pl.cl.)) titanium surfaces with nanostructures (Sample 5 (nano), Sample 2 (NaCl)) and without nano-structures (Sample 1, Sample 7 (pl.cl.));

FIG. 11B shows a magnification of the high resolution (5 µm) fluorescence scanner images of FIG. 11A (width of image corresponds to 1 mm)

Figure 12:
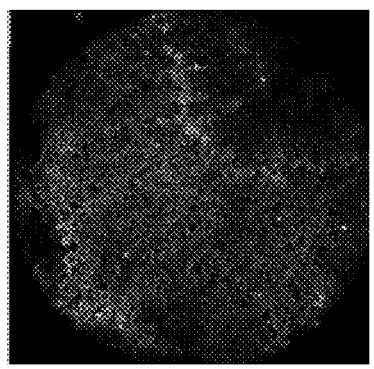
FIG. 12 shows a comparison of fluorescence scanner images of albumin on hydrophilic and hydrophobic sandblasted and acid-etched titanium surfaces (Sample 1, Sample 2 (NaCl), Sample 7 (pl.cl.) and Sample 5 (nano)) adsorbed from 15 µg/ml solution during 10 s, the width of the images corresponding to 5 mm.
Figure 12:
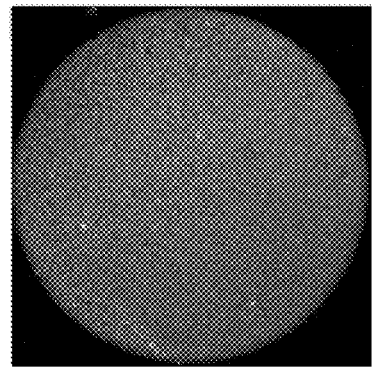
Figure 12:
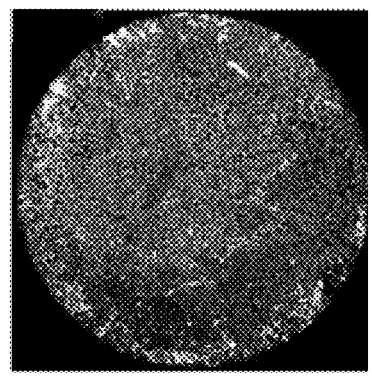
Figure 12:
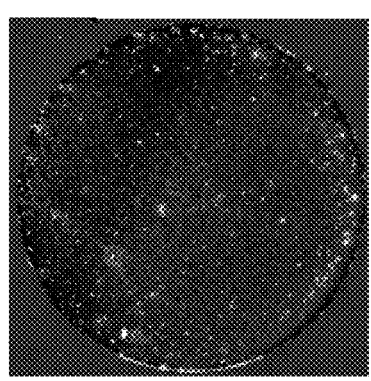
Figure 13:
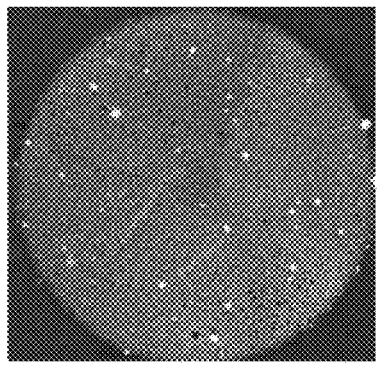
Figure 13:
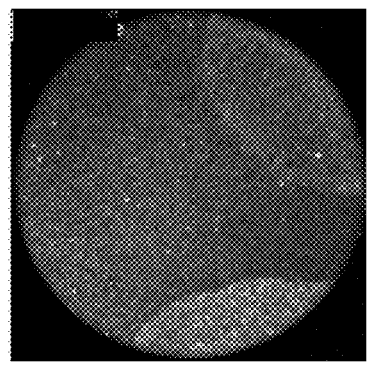
Figure 13:
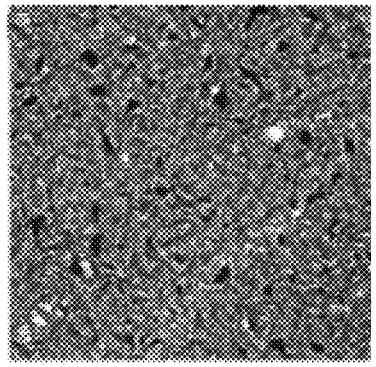
Figure 13:
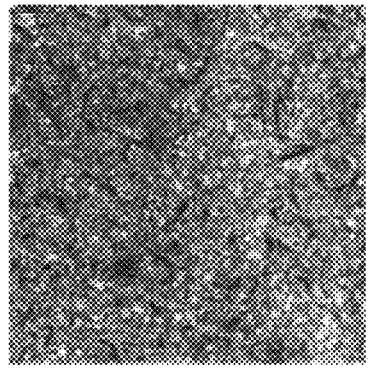

FIG. 12 shows a comparison of fluorescence scanner images of albumin on hydrophilic and hydrophobic sandblasted and acid-etched titanium surfaces (Sample 1, Sample 2 (NaCl), Sample 7 (pl.cl.) and Sample 5 (nano)) adsorbed from 15 µg/ml solution during 10 s, the width of the images corresponding to 5 mm;

FIG. 13 shows a brightness and contrast adjusted fluorescence scanner images of Sample 9 (TiZr NaCl) and Sample 2 (Ti NaCl) surfaces with fibrinogen adsorbed from a 7 µg/ml solution for 10 min, the width of the upper images corresponding to 5 mm and of the lower images corresponding to 1 mm;

Sandblasted and Acid Etched Titanium Surfaces

All values presented in FIG. 9 are normalized to the intensities measured for Sample 2 (NaCl) for the different proteins. The error bars indicate the standard deviation.

Generally, albumin, fibrinogen and fibronectin showed a similar adsorption behaviour.

The data acquired in the fluorescence intensity measurements clearly implied a strong influence of the presence of nanostructures on the measured fluorescence intensities (FIGS. 9 and 10). Those samples with nanostructures on their surface (Sample 2 (NaCl), Sample 5 (nano), Sample 6 (modA) and Sample 9 (TiZr NaCl)) showed increased intensities for all three proteins compared to the samples without nanostructures (Sample 1, Sample 4 (pmod)) (FIG. 9).

Hydrophilicity in combination with the presence nanostructures showed also a positive influence on protein adsorption: hydrophobic Sample 5 (nano) showed a clearly lower fluorescence intensity signal compared to Sample 2 (NaCl) although both surfaces seemed to exhibit equal nanotopography, thus a similar arrangement of nanostructures.

As can further be seen in FIG. 9, fluorescence intensity measurements also demonstrated a higher amount of adsorbed proteins on TiZr discs of Sample 9 (TiZr NaCl) surfaces relative to titanium discs of Sample 2 (Ti NaCl). The differences in adsorbed amounts of proteins were particularly significant for albumin (factor 2.5) and fibrinogen (factor 2).

With regard to the influence of storage time in aqueous solution it was found that the nanostructure on Sample 2 (NaCl) surfaces develops within about 2 weeks of storage. In case of Sample 4 (pmod), on the other hand, the nanostructure showed to be initially suppressed for about 2-3 months on Ti grade 2 and to grow for longer storage times.

The fibronectin adsorption on relatively newly fabricated Sample 10 discs (TiZr modMA) was monitored over three weeks (FIG. 10). During this time, an increase in intensity by a factor of about 2.5 was observed.

The results shown in FIG. 11 for sandblasted and acid etched titanium surfaces (Sample 1, Sample 2 (NaCl), Sample 5 (nano) and Sample 7 (pl.cl.)) were consistent with the results shown in FIG. 9: The samples with a nanostructure (Sample 2 (NaCl), Sample 5 (nano)) showed unambiguously more fluorescently labelled proteins on their surfaces.

Further could be seen that proteins adsorbed more homogeneously on hydrophilic surfaces: About 28% of Sample 5 (nano) surfaces were not covered by albumin (FIGS. 11C and 11G), whereas the protein distribution on Sample 2 (NaCl) discs (FIGS. 11D and 11H) was much more homogeneous.

The images with higher magnification (FIGS. 11E-H) showed an equal adsorption behavior on Sample 1 and Sample 5 surfaces in terms of protein distribution. On Sample 7 (pl.cl.) surfaces (FIGS. 11B and 11F) overall a very small amount of albumin was adsorbed. Interestingly, the mean intensities measured were the same for Sample 1 and Sample 7 (pl.cl.).

A similar adsorption tendency for albumin on Sample 1, Sample 2 (NaCl), Sample 7 (pl.cl.) and Sample 5 (nano) surfaces was also found when the samples were immersed for a much shorter time (10 s instead of 10 min) into a more concentrated (15 µg/ml instead of 3 µg/ml) albumin solution (FIGS. 12A-D).

The values of the relative intensities measured for albumin absorbed from 15 µg/ml solution for 10 s are listed in Table 7.

TABLE 7

|  | Sample 1 | Sample 2 | Sample 7 | Sample 5 |
|---|---|---|---|---|
| Disc 1 | 7481 | 35030 | 407 | 21725 |
| Disc 2 | 5781 | 34167 | 379 | 22225 |
| Disc 3 | 2828 | 36355 | 377 | 16920 |
| Mean | 5363 | 35184 | 388 | 20290 |
| Std | 2354 | 1102 | 17 | 2929 |

When compared with the above results obtained for 10 min adsorption time in 3 µg/ml albumin solution shown in FIG. 11, the shorter adsorption time of 10 s led to an even more heterogeneous appearance on the surface of Sample 1 discs (FIG. 12A). The surface on Sample 7 (pl.cl., FIG. 12B) showed a very low amount of adsorbed proteins.
TiZr Samples: Sample 8 and Sample 9 (NaCl)

As described for the titanium Sample 1, the surface on TiZr Sample 8 (FIG. 13, left images) showed much less adsorbed proteins compared to the discs of Sample 2 and Sample 9 (FIG. 13, right images) stored in NaCl before drying. However, size and shape of the dark areas without adsorbed proteins on TiZr Sample 8 differed from those observed for Ti Sample 1: On Ti Sample 1 discs, the uncovered area was more mesh-like, while smaller, separated dots were present on TiZr Sample 8 discs.

Higher homogeneity was also observed on the hydrophilic, nanostructured Sample 9 (TiZr NaCl) discs (FIG. 13, right images) compared to the surfaces on Sample 8 (TiZr) discs (FIG. 13, left images). The structures found on Sample 2 (Ti NaCl, FIG. 7B) was comparable to the one of Sample 9 (TiZr NaCl, FIG. 13, right images).
Biomechanical Pull-out Measurements FIG. 14 shows a diagram relating to the pull-out-force measured after 4 and 8 weeks of implantation, respectively;

FIG. 15 shows a diagram relating to the pull-out-force measured after 4 and 8 weeks of implantation, respectively;

Table 8 gives the measured pull-out-force in [N] after 4 weeks and 8 weeks of implantation. These data are visualized in the diagram of FIG. 14. As can be clearly seen from FIG. 14, pull-out-forces increased with the implantation time. Generally, Sample 2 (NaCl) implants showed the highest pull-out-forces.

TABLE 8

|  | Parameter | pull out force [N]—4 weeks | pull out force [N]—8 weeks |
| --- | --- | --- | --- |
| Sample 1 | n | 12 | 13 |
|  | Mean ± SD | 40.4 ± 11.5 | 82.4 ± 39.8 |
|  | Median (Range) | 38.45 | 77.2 |
|  |  | (25.0 to 58.8) | (21.2 to 194.0) |
| Sample 2 | n | 12 | 12 |
| (NaCl) | Mean ± SD | 85.3 ± 24.9 | 130.1 ± 26.6 |
|  | Median (Range) | 83.9 | 136.3 |
|  |  | (51.0 to 144.0) | (87.0 to 166.0) |
| Sample 4 | n | 12 | 13 |
| (pmod) | Mean ± SD | 67.8 ± 22.6 | 122.0 ± 25.5 |
|  | Median (Range) | 67.45 | 120.9 |
|  |  | (32.3 to 94.6) | (80.1 to 168.8) |
| Sample 5 | n | 12 | 13 |
| (nano) | Mean ± SD | 61.2 ± 18.7 | 97.6 ± 27.4 |
|  | Median (Range) | 62.7 | 95 |
|  |  | (31.8 to 95.5) | (57.8 to 148.7) |

After 4 weeks, Sample 2 (NaCl) implants revealed a significant higher pull-out force than Sample 1 and Sample (nano) implants. Pull-out values for Sample 2 (NaCl), Sample 4 (pmod) and Sample 5 (nano) implants are significantly higher than for Sample 1 implants.

Generally, implant retention increases with time. As illustrated in FIG. 15, at 4 weeks healing time, the functional attachment was weaker than 8 weeks after implantation. At 8 weeks healing time, the mean pull-out values representing the tensile force binding the implant to bone increases with a factor of about 2 compared to the 4 weeks result.

A significantly different retention in bone was demonstrated between the Sample 1 discs and the discs of Sample 2 (NaCl), Sample 4 (pmod) and Sample 5 (nano) following implantation and 4 or 8 weeks of healing time (FIGS. 14, 15) and showing a significantly higher retention.
Discussion The present examples encompass discrimination of different surface modification steps of importance for the formation of nanostructures.

The chemical analysis as well as the result that also the Sample 3 (water) surfaces showed the presence of nanostructures excludes the possibility that the nanostructures were crystallized NaCl. The observed increase of the oxide layer thickness may be explained by the dense layer of nanoparticles, a further indication that the composition of the nanoparticles is $TiO_2$. Their needle-like shape indicated that the nanostructures were mainly composed of rutile crystals.

Interestingly, the TiZr surfaces (Sample 9 (NaCl)) showed a slightly lower oxide layer thickness compared to the Ti surfaces with the presence of a nanostructure. This trend is in agreement with the lower density of nanoparticles observed in the SEM images.

The limited probing depth of XPS of about 10 nm in case of $TiO_2$ leads to an underestimation of the thickness of the $TiO_2$ if the nanostructure is present. The errors indicated for the calculated oxide layer thickness are only statistical errors. However, systematic errors due to wrong assumptions or inconsistencies in the model are expected to be dominant over the statistical errors. Nevertheless, the as calculated values allow a reasonable (relative) comparison of the nominal oxide layer thickness of the different types of samples. The thickness of the $TiO_2$ layer showed the following trend: Sample 2 (NaCl)>Sample 5 (nano)>Sample 4 (pmod)>Sample 1

The Sample 3 storage in water compared to NaCl solution did not influence the surface roughness, nanostructure formation or wettability. Nor did the Y-sterilization have any influence on the surface properties.

Sample 5 (nano) demonstrated that, once evolved, the nanoparticles were stable on the surface, also under dry conditions. However, acid-etching in combination with storage in aqueous solution was found to be essential for the nanostructure formation. In this regard, the dissociative adsorption of water seems to play a crucial role and Ti diffusion has to take place for the growth of the nanostructure. The diffusion behaviour of Ti and TiZr was expected to be different, which was confirmed by the different nanostructure morphology and density. The latter can be explained by the better corrosion properties of TiZr than Ti. The different corrosion properties might result in less diffusion on the TiZr outermost surface, resulting in a lower density of nanostructures.

The plasma cleaning severely slowed down the formation of the nanoparticles. The onset of nanostructure formation on Sample 4 (pmod) discs was only observed after several months of storage in aqueous solution. The morphology of the nanostructure was different in case of the Sample 4 (pmod) discs compared to the Sample 2 (NaCl) discs. From XPS measurements it is known that oxygen plasma cleaning leads to a slight increase of the oxide layer thickness. Thus, the plasma cleaning modifies the oxide layer to a certain extent resulting in hindrance of the nanostructure growth. Probably, the plasma cleaning heals defects in the oxide layer yielding a more homogeneous oxide layer with lower numbers of defects. This might protect the surface from further oxidation and hence fewer nanocrystals will form. Thus, it is assumed that potential nucleation centres are either diminished or made inactive due to the plasma treatment leading to a passivation of the surface.

These results show the importance of acid-etching in conjunction with the storage in aqueous solution for the formation of the nanostructure. A relatively small chemical modification of the surface due to the plasma treatment leads to a distinctly different behaviour in terms of the nanostructure formation.

It should be noticed that nanostructures on different Ti and TiZr samples vary mainly in density but, to a smaller degree, also in their shapes.

The protein adsorption tests, with particular focus on Ti and TiZr samples, demonstrated that nanostructures have a highly positive effect on protein adsorption. This effect is not simply based on the enlargement of the surface area but on the nanostructures acting as retention sites due to increased electrostatic and van der Waals forces.

The positive effect of the hydrophilicity was particularly evident for samples with nanostructures in terms of a more homogeneous coverage of hydrophilic surfaces.

Slightly different adsorption patterns were observed for the hydrophobic Sample 8 (TiZr) discs compared to the purely titanium Sample 1 discs.

In case of hydrophobic surfaces with nanostructures, the proteins adsorbed in a manner forming island like structures, whereas for hydrophilic surfaces with nanostructures the proteins covered the surface almost homogeneously. Without wanting to be bound by the theory, it is assumed that the areas without adsorbed proteins on hydrophobic surfaces are a result of deficient surface wetting, i.e. the presence of tiny air bubbles at the interface. A second hypothesis would be that these islands are still covered by hydrocarbons that could not be replaced by proteins within the adsorption time in spite of surface wetting.

The invention claimed is:

1. Process for providing structures for an improved protein adherence on the surface of a body, said process comprising
    a) providing a basic body made of titanium or a titanium alloy,
    b) acid-etching the basic body,
    c) storing the acid-etched basic body in pure water or an aqueous solution having a pH in a range of from 4 to 6 for at least two days, whereby nanostructures are formed on the surface of the basic body,
    d) drying the basic body with the nanostructures formed on its surface, and
    e) storing the basic body in a dry environment for at least one day after the drying according to d).

2. Process according to claim 1, wherein the titanium alloy is a titanium zirconium alloy.

3. Process according to claim 1, further comprising roughening the basic body by sand-blasting prior to the acid-etching according to b).

4. Process according to claim 1, wherein the acid-etching according to b) is performed with a mixture of HCl and $H_2SO_4$.

5. Process according to claim 1, further comprising cleaning the basic body using a plasma prior to the storing according to c).

6. Process according to claim 1, wherein the basic body is stored in a dry environment for at least two days after the drying according to d).

7. Process according to claim 1, wherein the formation of nanostructures on the surface of the basic body is an additive process and the nanostructures are formed of a material based on the material of the basic body.

8. Process according to claim 7, wherein the nanostructures comprise titanium oxide.

* * * * *